United States Patent [19]

Cummings

[11] Patent Number: 5,369,100
[45] Date of Patent: Nov. 29, 1994

[54] CHEMICALLY STABLE COMPACTED PARTICLES CONTAINING INSECTICIDAL PHOSPHOROAMIDOTHIOATES AND METHODS FOR THE MANUFACTURE AND USE THEREOF

[75] Inventor: Gary L. Cummings, Moraga, Calif.

[73] Assignee: Valent U.S.A. Corporation, Walnut Creek, Calif.

[21] Appl. No.: 950,295

[22] Filed: Sep. 24, 1992

Related U.S. Application Data

[63] Continuation-in-part of Ser. No. 856,485, Mar. 24, 1992, which is a continuation-in-part of Ser. No. 674,857, Mar. 25, 1991, abandoned.

[51] Int. Cl.$^5$ .................. A01N 57/02; A01N 57/04; A01N 59/02
[52] U.S. Cl. .................. 514/120; 514/137; 514/75; 424/710
[58] Field of Search .......... 514/75, 120, 137; 424/710

[56] References Cited

U.S. PATENT DOCUMENTS

| | | | |
|---|---|---|---|
| 378,583 | 2/1888 | Feustell | 424/704 |
| 3,585,022 | 6/1971 | Gray, Jr. et al. | 504/187 |
| 3,622,677 | 7/1971 | Short | 424/361 |
| 3,716,600 | 2/1973 | Magee | 558/178 |
| 3,845,172 | 10/1974 | Magee | 558/178 |
| 3,914,417 | 10/1975 | Magee | 424/219 |
| 3,919,416 | 11/1975 | Cosby | 424/162 |
| 5,075,058 | 12/1991 | Chan et al. | 264/118 |
| 5,100,667 | 3/1992 | Chan et al. | 424/405 |

FOREIGN PATENT DOCUMENTS 0415609 3/1991 European Pat. Off.
91/11104 8/1991 WIPO.

*Primary Examiner*—Gary E. Hollinden
*Assistant Examiner*—Mary C. Cebulak
*Attorney, Agent, or Firm*—Sughrue, Mion, Zinn, Macpeak & Seas

[57] ABSTRACT

The present invention is directed to an insecticidal composition including irregularly shaped to spherically shaped particles prepared by compaction, in the absence of a binder, of an admixture including ammonium sulfate and at least one insecticidal compound of the formula:

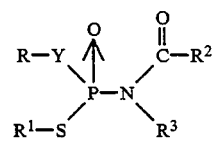

wherein R and $R^1$ individually are an alkyl, alkenyl or alkynyl group containing up to 6 carbon atoms, $R^2$ is hydrogen, an alkyl group containing 1 to 18 carbon atoms, a cycloalkyl group containing 3 to 8 carbon atoms, an alkenyl group containing 2 to 18 carbon atoms or an alkynyl group containing 3 to 18 carbon atoms, $R^3$ is hydrogen or an alkyl group containing 1 to 6 carbon atoms, and Y is oxygen or sulfur. The present invention is also directed to methods for manufacturing such particles and for killing insects with such particles.

16 Claims, 1 Drawing Sheet

CHEMICALLY STABLE COMPACTED PARTICLES CONTAINING INSECTICIDAL PHOSPHOROAMIDOTHIOATES AND METHODS FOR THE MANUFACTURE AND USE THEREOF

CROSS-REFERENCE TO RELATED APPLICATIONS

This application is a continuation-in-part of U.S. application Ser. No. 07/856,485 filed Mar. 24, 1992, which in turn is a continuation-in-part of U.S. application Ser. No. 07/674,857 filed Mar. 25, 1991, now abandoned.

BACKGROUND OF THE INVENTION

1. Field of the Invention

The present invention is directed to irregularly shaped to spherically shaped compacted particles containing insecticidal phosphoroamidothioates and to methods for manufacturing and using the compacted particles. In particular, the present invention is directed to chemically stable, irregularly shaped to spherically shaped, compacted particles of insecticidal phosphoroamidothioates which contain ammonium sulfate. The present invention is also directed to methods for manufacturing compacted particles containing insecticidal phosphoroamidothioates and ammonium sulfate and for killing insects through the use of such particles.

2. State of the Art

Insecticidal compositions in various forms have been developed for diverse applications. The method of preparation of the insecticidal composition is largely determined by the physical and chemical nature of the insecticide and the intended use and method of application of the insecticide to the area to be treated.

Certain phosphoroamidothioates and phosphoroamidodithioates ("phosphoroamidothioates") are known in the art as having excellent insecticidal activity against a variety of insects and in a variety of environments. A particularly important commercial insecticide within these classes of compounds is the insecticide acephate (generic name) or Orthene ® (tradename), which can be systemically taken up by a plant so that insects which feed and/or live on the plant are killed, in addition to those insects which directly ingest or are contacted by the insecticide. Acephate and related compounds are described in U.S. Pat. Nos. 3,716,600, 3,845,172 and 3,914,417, which disclose that in addition to their insecticidal properties, the compounds possess very low mammalian toxicity. Orthene ® is commercially produced as a technical grade chemical of about 97 to 99.5% purity.

One method of formulating technical grade phosphoroamidothioates for commercial use is to mix the technical grade powder with an anti-caking agent, such as fumed silica, and a wetting agent. The wetting agent is utilized to wet the insecticide and the anti-caking agent, and the anti-caking agent is used to prevent agglomeration of the insecticide in its container. This formulation of insecticide can be applied to crops as a spray solution or as a dust.

The use of phosphoroamidothioates as powders allows for relatively high concentrations of insecticide to be applied to a treatment area, but the powder application suffers from various disadvantages. First, the finely divided particles of active spray may be carried by air currents into areas where harmful effects may occur. In addition, it is difficult to apply sprays or dusts to the soil surface or to lower areas of plants when dense foliage must be penetrated. Also, the powder has a bad odor. Additionally, in its powder form, it becomes airborne easily, and it is perceived as a health hazard. Finally, powdered phosphoroamidothioates suffer from chemical stability problems due to hydrolytic and catalytic driven degradation, which shortens the shelf life of the powdered insecticide.

While the use of acephate in granular form (e.g., pellets) would overcome some of the inherent difficulties involved in using sprays or dusts, granular formulations suffer from various problems.

One problem in granular compositions is the presence of dry additives and processing aids such as diluents, lubricants, flowability agents, surfactants, etc., which have been determined to aggravate the chemical stability problems of insecticidal phosphoroamidothioates. In turn, the lack of chemical stability for granular insecticidal phosphoroamidothioates interferes with the commercial feasibility of such formulations.

In addition, and importantly, binders have been used to make granular insecticidal phosphoroamidothioates by pellet or adhesion technologies. However, binders add to product cost, adversely affect the chemical stability of insecticidal phosphoroamidothioates and cause problems in processing. Also, granules containing binders can have problems with water insolubility, thereby limiting their use to direct application (placing the granules on or around each plant), which can be impractical for some commercial farming ventures.

Furthermore, methods such as pan granulation and extrusion (pelletizing), which have been used to make granules, have adverse effects on insecticidal phosphoroamidothioates like Orthene ®.

Pan granulation employs water, and the granules which are initially produced contain a significant amount of water. As a result, a dryer is used to remove the water from the granules. However, Orthene ® degrades in water and is heat-sensitive, so the use of pan granulation is disadvantageous for producing Orthene ® formulations.

In regard to pelletization processes, U.S. Pat. Nos. 5,075,058 and 5,100,667 describe processes for pelletizing formulations containing insecticides such as phosphoroamidothioates. In particular, U.S. Pat. No. 5,075,058 discloses a process for forming pellets by extruding a mixture of Orthene ®, a second active ingredient, and optional components such as a limited amount of ammonium sulfate, and U.S. Pat. No. 5,100,667 exemplifies a process for forming pellets of Orthene ® alone or in combination with a surfactant and ammonium sulfate using a pellet mill. However, pellet mills or extruders used to form pellets from mixtures containing Orthene ® can generate heat. As noted above, Orthene ® is heat-sensitive, so pelletizing is disadvantageous for producing Orthene ® formulations. Also, extruded or pellet forms typically produce regularly or cylindrically shaped granules which are difficult to apply directly to the ground with conventional granule application equipment. Further, U.S. Pat. Nos. 5,075,058 and 5,100,667 neither teach nor suggest that formulations which contain effectively only insecticidal phosphoroamidothioates and ammonium sulfate have enhanced chemical stability.

Thus, there is a need in the art for low cost, highly effective, chemically stable insecticidal phosphoroamidothioate granular formulations and for processes for manufacturing the same.

SUMMARY OF THE INVENTION

In view of the above problems in the art, one object of the present invention is to provide chemically stable insecticidal phosphoroamidothioate formulations.

A second object of the present invention is to provide insecticidal phosphoroamidothioate formulations which can be applied either directly to plants or dissolved into water to the soil adjacent to form a spray solution.

A third object of the present invention is to provide insecticidal phosphoroamidothioate formulations which are safer and which have greatly reduced odor.

A fourth object of the present invention is to provide insecticidal phosphoroamidothioate formulations having excellent attrition resistance.

A fifth object of the present invention is to provide insecticidal phosphoroamidothioate formulations having excellent dissolution properties.

A sixth object of the present invention is to provide insecticidal phosphoroamidothioate formulations which are easy to manufacture.

A seventh object of the present invention is to provide a method for manufacturing such insecticidal phosphoroamidothioate formulations.

An eighth object of the present invention is to provide a method for using such insecticidal phosphoroamidothioate formulations.

The above objects and other objects are obtained by the present invention as set forth below.

In one of its aspects, the present invention is directed to an insecticidal composition comprising irregularly shaped to spherically shaped particles prepared by compaction, in the absence of a binder, of an admixture comprising ammonium sulfate and at least one insecticidal compound of the formula:

wherein R and $R^1$ individually are an alkyl, alkenyl or alkynyl group containing up to 6 carbon atoms, $R^2$ is hydrogen, an alkyl group containing 1 to 18 carbon atoms, a cycloalkyl group containing 3 to 8 carbon atoms, an alkenyl group containing 2 to 18 carbon atoms or an alkynyl group containing 3 to 18 carbon atoms, $R^3$ is hydrogen or an alkyl group containing 1 to 6 carbon atoms, and Y is oxygen or sulfur.

In another of its aspects, the present invention is directed to a method for manufacturing an insecticidal composition, comprising (a) mixing ammonium sulfate and at least one insecticidal compound of the formula:

wherein R and $R^1$ individually are an alkyl, alkenyl or alkynyl group containing up to 6 carbon atoms, $R^2$ is hydrogen, an alkyl group containing 1 to 18 carbon atoms, a cycloalkyl group containing 3 to 8 carbon atoms, an alkenyl group containing 2 to 18 carbon atoms or an alkynyl group containing 3 to 18 carbon atoms, $R^3$ is hydrogen or an alkyl group containing 1 to 6 carbon atoms, and Y is oxygen or sulfur in a mixer to form a mixture of the ammonium sulfate and the at least one insecticidal compound;

(b) compacting the mixture in a compactor to produce a compacted formulation;

(c) crushing the compacted formulation to form irregularly shaped to spherically shaped compacted particles; and (d) screening the compacted particles through a screen to separate oversized particles and undersized particles from particles having a desired particle size.

In another of its aspects, the present invention is directed to a method for killing insects which comprises applying to an area to be treated an insecticidally effective amount of irregularly shaped to spherically shaped particles prepared by compaction, in the absence of a binder, of an admixture comprising ammonium sulfate and at least one insecticidal compound of the formula:

wherein R and $R^1$ individually are an alkyl, alkenyl or alkynyl group containing up to 6 carbon atoms, $R^2$ is hydrogen, an alkyl group containing 1 to 18 carbon atoms, cycloalkyl containing 3 to 8 carbon atoms, an alkenyl group containing 2 to 18 carbon atoms or an alkynyl group containing 3 to 18 carbon atoms, $R^3$ is hydrogen or an alkyl group containing 1 to 6 carbon atoms, and Y is oxygen or sulfur;

wherein the at least one insecticidal compound is present in the particles in an amount of from about 1 to about 25% by weight, In another of its aspects, the present invention is directed to a method for killing insects which comprises (a) preparing irregularly shaped to spherically shaped particles by compaction, in the absence of a binder, of an admixture comprising ammonium sulfate and at least one insecticidal compound of the formula:

wherein R and $R^1$ individually are an alkyl, alkenyl or alkynyl group containing up to 6 carbon atoms, $R^2$ is hydrogen, an alkyl group containing 1 to 18 carbon atoms, a cycloalkyl group containing 3 to 8 carbon atoms, an alkenyl group containing 2 to 18 carbon atoms or an alkynyl group containing 3 to 18 carbon atoms, $R^3$ is hydrogen or an alkyl group containing 1 to 6 carbon atoms, and Y is oxygen or sulfur;

wherein the at least one insecticidal compound is present in the particles in an amount of from about 1 to about 97% by weight; and (b) dissolving the particles into water to form an insecticidal solution;

(c) spraying the insecticidal solution in an insecticidally effective amount onto an area to be treated.

DETAILED DESCRIPTION OF THE INVENTION

Figure 1:
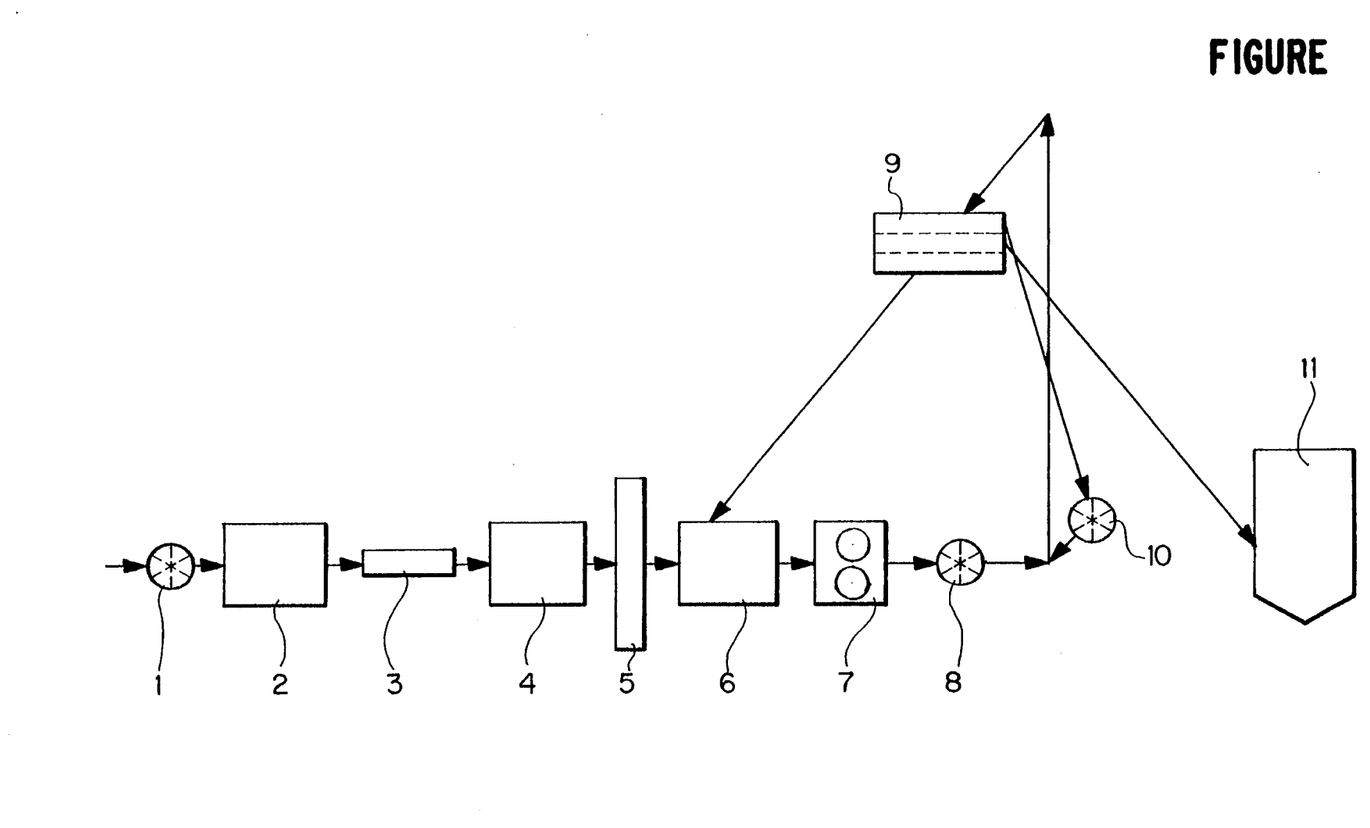
The FIGURE shows a schematic diagram of a possible commercial unit for producing the irregularly shaped to spherically shaped compacted particles of the present invention.

An important feature of the present invention is the discovery that formulations which contain insecticidal phosphoroamidothioates in part should contain effectively only ammonium sulfate as the remainder of the composition if good chemical stability is to be achieved. If the ammonium sulfate is replaced with a seemingly similar compound (e.g., ammonium phosphate or potassium sulfate) or a commonly used filler (e.g., bentonite, diatomaceous earth, or attapulgite), the chemical stability of the formulation is adversely affected. Also, the presence of other components in addition to the insecticide phosphoroamidothioate and the ammonium sulfate causes the chemical stability of the formulation to degrade, with the degree of degradation increasing with increasing amounts of other components.

This discovery is important, because it is desirable to have a wide range of formulations in terms of insecticidal strength, and it is desirable for all the formulations to be chemically stable. For example, if the formulation is to be applied in particle form, the amount of insecticidal phosphoroamidothioate present in the formulation might be only 5 to 15% by weight, so the balance must be effectively ammonium sulfate for the formulation to be chemically stable. As another example, if the formulation is to be mixed with water to form a solution, the amount of insecticide phosphoroamidothioate present in the formulation might be 50 to 95% by weight, so the balance must be effectively ammonium sulfate for the formulation to be chemically stable. Of course, if the formulation is 100% insecticide phosphoroamidothioate, no ammonium sulfate is present, in which case the chemical stability of the formulation depends on the method by which it is prepared, with compaction resulting in the best chemical stability because no water is used and no significant heat is generated in the manufacturing process. Also, when additives such as lubricants and flowability aids need to be used, they should be kept to a minimum to minimize the degradation of acephate.

Another important feature of the present invention is the discovery that an insecticidal phosphoroamidothioate by itself or mixed with ammonium sulfate can be compacted to form particles of a sufficient hardness such that the presence of a binder is not needed. By eliminating the need for a binder, the present invention avoids degradation of the chemical stability of the formulation. Also, product cost can be reduced, and the formulation can be manufactured more easily and efficiently.

Thus, one aspect of the present invention is directed to an insecticidal composition comprising irregularly shaped to spherically shaped particles prepared by compaction, in the absence of a binder, of an admixture comprising at least one insecticide phosphoroamidothioate and ammonium sulfate. Also, the present invention is directed to an insecticidal composition comprising irregularly shaped to spherically shaped particles prepared by compaction, in the absence of a binder, of at least one insecticide phosphoroamidothioate.

The term "phosphoroamidothioate" refers to a compound or a mixture of compounds of the formula:

wherein R and $R^1$ individually are an alkyl, alkenyl or alkynyl group containing up to 6 carbon atoms, $R^2$ is hydrogen, an alkyl group containing 1 to 18 carbon atoms, a cycloalkyl group containing 3 to 8 carbon atoms, an alkenyl group containing 2 to 18 carbon atoms or an alkynyl group containing 3 to 18 carbon atoms, $R^3$ is hydrogen or an alkyl group containing 1 to 6 carbon atoms, and Y is oxygen or sulfur.

Particularly preferred compounds are those in which R and $R^1$ are independently a methyl, ethyl, allyl or alkenyl group; $R^2$ is H or an alkyl group; $R^3$ is hydrogen; and Y is oxygen. The most preferred compound is that in which R, $R^1$, and $R^2$ are methyl groups, $R^3$ is hydrogen and Y is oxygen. Compounds of the above formula may be prepared as described in U.S. Pat. Nos. 3,176,600, 3,845,172 and 3,914,417, which are incorporated herein by reference in their entirety. Likewise, acephate (R, $R^1$, $R^2$ are $CH_3$; $R^3$ is hydrogen and Y is oxygen) is commercially available from Chevron Chemical Company, San Ramon, Calif. (e.g., Orthene® 90S (90% acephate), Orthene® 80S (80% acephate) and Orthene® 75S (75% acephate)).

One or a mixture of the above compounds forms the active insecticidal component in the formulation of this invention. The amount of insecticidal component in the invention formulation can be varied as desired according to use, although in essentially all cases the insecticidal component is present in the particle in an amount of from at least about 1 weight percent, based on the total weight of the formulation.

If the formulation is to be applied directly as particles, the insecticidal component will be present in an amount of from about 1 to about 25 weight percent, based on the total weight of the formulation. Preferably, the insecticidal component will be present in an amount of from about 1 to about 17 weight percent, more preferably the insecticidal component will be present in an amount of from about 1 to about 15 weight percent, and still more preferably the insecticidal component will be present in an amount of from about 5 to about 15 weight percent. Most preferably, the insecticidal component will be present in an amount of about 15 weight percent.

If the formulation is to be mixed with water to form a solution, the insecticidal component will be present in an amount of from about 1 to about 100 weight percent, based on the total weight of the formulation- Preferably, the insecticidal component will be present in an amount of from about 1 to about 97 weight percent. More preferably, the insecticidal component will be present in an amount of from about 50 to about 95 weight percent. In a preferred range, the insecticidal component will be present in an amount of from 50 to about 75 weight percent.

The term "processing aids" refers to, e.g., lubricants and flowability aids, which can be used as needed in preparing the formulations.

Lubricants can be used as needed in the preparations to permit the formulation to be released more readily from the compactor rolls in the compaction process. Suitable lubricants include, by way of example, magnesium stearate, calcium stearate, zinc stearate, silicon emulsions, and the like. The particular lubricant employed is not significant and, when employed, generally from about 0.2 to about 5 weight percent and preferably from about 0.2 to about 1 weight percent of lubricant is used, based on the total weight of the formulation. It is desirable to minimize the use of lubricants to minimize the degradation of chemical stability Flowability aids ("flow aids") also can be used as needed in the formulation to permit the formulation to flow more readily during the processing of the compacted particles, i.e., during mixing, grinding, and feeding the compactor. Suitable flowability aids include, by way of example, colloidal silica particles, micronized clays, or fillers such as bentonite, kaolin, diatomite, attapulgite, and the like. The particular flowability aid employed is not significant and, when employed, generally from about 0.5 to about 5 weight percent of flowability aid is used, based on the total weight of the formulation. Again, it is desirable to minimize the use of flowability aids to minimize the degradation of chemical stability.

As noted previously, binders are desirably not used in the present invention because the compacted particles have a sufficient hardness without binders and because binders can adversely affect chemical stability, add to production cost, and cause problems during the manufacturing of the particles. However, if binders are used as a processing aid, they may be selected from, by way of example, corn starch, polymers, natural gums, and the like. The specific binder employed is not significant and, when employed, generally from about 0.5 to about 6 weight percent, preferably not more than about 5 weight percent, more preferably not more than about 4 weight percent, most preferably not more than about 3 weight percent, is used.

Also, other additives can be used as needed. For example, surfactants can be employed to affect the rate of particle disintegration after applications, and the amount thereof can be from about 0.2 to about 5 weight percent, preferably not more than about 4 weight percent, more preferably not more than about 3 weight percent, still more preferably not more than about 2 weight percent, based on the total weight of the formulation. Most preferably, a surfactant is not used at all, since it is not needed in the present invention. Deodorants (as well as reodorants) can be used to counter the odor of acephate, and the amount thereof can be from about 0.05 to about 2 weight percent, based on the total weight of the formulation. Again, it is noted that the presence of additives should be minimized to minimize the degradation of chemical stability.

If additives are used in the formulation, the total amount thereof preferably should not exceed about 6 weight percent, more preferably it should not exceed about 5 weight percent, and still more preferably it should not exceed 4 weight percent, based on the total weight of the formulation, for purposes of minimizing the degradation of chemical stability.

The admixture is processed into particles by a compaction. Specifically, the admixture is generally mixed to uniformity, ground with a mill, compacted at a high pressure, crushed, and screened.

Each of the operations in the manufacturing process of the present invention is discussed below.

Mixing operations are carried out to ensure that the particles which are ultimately produced have the desired uniform composition. Examples of mixers which are suitable for the present invention are powder mixers, including Marion paddle mixers, and ribbon blenders.

Crushing operations are preferably carried out to provide a desired material size for the compacting step and elsewhere in the process. Examples of commercially-available mills which are suitable for the present invention include a Sprout Bauer Model 38-123 mill, a Fitz hammermill, a Micropul #2DH hammermill, a Pulvachron PC-38 air classifying mill, a Jacobsen 2615 Full Nelson crusher, and a Reitz RD-8 disintegrator.

Compacting operations are carried out to provide sufficiently hard formulations without the need for binders and without the use of water or the significant generation of heat, which adversely affect the chemical stability of the product. The compaction pressure is preferably at least about 4,000 psig, more preferably at least about 6,500 psig, and particularly preferably at least about 8,000 psig, and it can be as high as 15,000 psig or even higher. The pressure which is used can depend on the desired properties of the product being produced, with lower pressures being sufficient for particles intended for dissolution for use in solutions and higher pressures being employed for particles intended for direct application to the area to be treated. Examples of commercially-available compactors which are suitable for the present invention include Bepex MS compactors (e.g., a Bepex MS150 compactor), a Chilsonator M-83 compactor, a Carver press, and a roller compactor manufactured by Freund Industrial Co., Ltd. The compacting operation can form sheets or rods of the formulation, which are then crushed to form the compacted particles.

Screening operations are carried out to provide a product with a specific particle size range. Suitable examples of commercially-available screeners include a Rotex 521 three deck screener and a Cason 48-inch, two screen screener.

The particles of this invention are preferably from about 4 mesh to about 60 mesh in size and more preferably from about 16 mesh to about 48 mesh in size. In one preferred embodiment, the particles of this invention are from 14 mesh to 40 mesh in size. The particle shape is irregular to spherical, because the compacted formulation is shattered to form the particles, and thus is different from the regular shape of granules produced by, e.g., pelletization.

A possible commercial embodiment of the manufacturing process is shown in the FIGURE. In the process, ammonium sulfate is fed to mill 1 (e.g., a Sprout Bauer Model 38-123 mill), where it is initially ground. The ground ammonium sulfate is fed to a paddle mixer 2 (e.g., a Marion paddle mixer), where insecticidal phosphoroamidothioates and any processing aids are added and the initial blending of the materials is conducted. The blended material is then fed to a turbolizer 3 to remove any lumps in the material, which is subsequently fed to a paddle mixer 4 for further blending and then to a mill 5 (e.g., a Pulvachron PC-38 air classifying mill) for pulverization. The pulverized material is fed to a paddle mixer 6 to ensure that the feed to compactor 7 has a uniform composition. The compacted formulation provided by compactor 7 (which can be, e.g., a Bepex MS150 compactor) is fed to a mill 8 (e.g., a Jacobsen 2615 Full Nelson crusher) to crush the formulation into irregularly shaped particles. The particles are fed to a screener 9 (e.g., a three deck Rotex 521 screener) for screening in order to separate particles having a desired particle size from undersized and oversized particles. The undersized particles are returned to paddle mixer 6 to be blended into the composition being fed to the compactor 7. The oversized particles are fed to a mill 10 (e.g., a Reitz RD-8 disintegrator) for disintegration, and the disintegrated particles which are produced are sent to screener 9 for screening. The particles having the desired particle size are sent to bin 11 for storage.

As can be seen from the description of the possible commercial embodiment of the manufacturing process as set forth above, the present invention includes within its scope a recycle feature to provide efficient use of the feed materials. That is, all of the undersized and oversized crushed, compacted particles are recycled into an appropriate stage of the production process. By contrast, in a compaction process without recycling, generally only about 40–60% of the particles produced have a desired size after one pass; recycling enables all (100%) of the feed to be ultimately formed into the desired particles. Further, it is important to note that when a binder is not used in making the particles, the recycled material has the same composition as the original feed to the compactor and does not require further milling or processing before being added to the compactor feed, which is advantageous for ease of recycling and processing.

As set forth above, the ammonium sulfate imparts chemical stability to insecticidal phosphoroamidothioates. The term "chemical stability" can be considered as meaning that the amount of the insecticidal phosphoroamidothioates in the formulation does not diminish by more than about 10% when stored under accelerated storage conditions of 28 days at 50°–55° C. as compared to the amount of the phosphoroamidothioates in the formulation at zero time (e.g., prior to storage). Under these accelerated conditions, insecticidal phosphoroamidothioate particles which do not result in diminished amounts of the phosphoroamidothioate under these accelerated conditions evidence the fact that such particles will possess excellent long term storage stability under ambient conditions. Without being limited to any theory, it is believed that in some way the use of ammonium sulfate interferes with the degradation of the phosphoroamidothioate, thereby imparting chemical stability to the particles.

Once formulated, the particles are useful in a method for controlling insects by application of the particles onto the insecticidal habitat. In general, the particles can be applied onto the habitat in an amount effective to be insecticidal to the insects. In a preferred embodiment, the particles are applied at a rate of at least about 0.5 lb (0.227 kg) acephate per acre and more preferably at a rate of from about 0.5 lb (0.227 kg) to about 2.0 lbs (0.909 kg) acephate per acre (0.004 square kilometer). Obviously, the amount of particles to be applied per acre (0.004 square kilometer) will depend upon the concentration of acephate in the particles. Thus, for example, particles containing 10% acephate will need to be applied at 5 lbs (2.27 kg) per acre (0.004 square kilometer) to achieve a dosage of 0.5 lb (0.227 kg) acephate per acre (0.004 square kilometer).

In a preferred example of the solution application, invention particles are dissolved in from about 10 gallons (37.8 liters) to about 50 gallons (189 liters) of water for application per acre, such that at least about 0.5 lb (0.227 kg) acephate per acre and more preferably from about 0.5 lb (0.227 kg) to about 2.0 lbs (0.909 kg) acephate is applied per acre (0.004 square kilometer). Obviously, the amount of particles to be dissolved in the water will depend upon the concentration of acephate in the particles. Thus, for example, 1 (0.454 kg) of particles containing 50% acephate will need to be dissolved in from about 10 gallons (37.8 liters) to about 50 gallons (189liters) of water to achieve a dosage of 0.5 lb (0.227 kg) acephate per acre (0.004 square kilometer), when from about 10 gallons (37.8 liters) to about 50 gallons (189 liters) of insecticidal solution is sprayed per acre (0.004 square kilometer).

The following examples illustrate specific embodiments of the invention but should not be construed as limiting the scope of the claims in any way. All parts, percents, ratios and the like are by weight unless otherwise indicated. All preparations in the Examples were prepared by the compaction techniques discussed herein.

EXAMPLES

Example 1

The purpose of this example is to demonstrate the significance of employing at most only a small amount of processing aids with an effective amount of ammonium sulfate in the insecticidal phosphoroamidothioate particle in order to impart chemical stability to the particle.

Five different tests were conducted in order to determine the effect of processing aids on insecticidal phosphoroamidothioate stability in particles.

A. The first test was conducted as follows:

Two different particle formulations containing acephate (Orthene®) , ammonium sulfate and either 1 weight percent of processing aids or 6 weight percent of processing aids were prepared and tested under accelerated storage conditions. Specifically, admixtures were prepared as shown in Table 1A below:

TABLE 1A

|  | Weight Percent | |
| --- | --- | --- |
|  | Particle A | Particle B |
| Orthene ® 90-S[1] | 11.1 | 11.1 |
| Cab-O-Sil M-5 | 0.5 | 0.5 |
| Corn Starch | — | 5.0 |
| Magnesium stearate | 0.5 | 0.5 |
| Ammonium Sulfate | 87.9 | 82.9 |

[1]Orthene ® 90-S contains 90% acephate with the remainder being inerts such as silica and surfactant.

The admixtures were then formulated into particles by first coarse grinding and uniformly mixing the admixture. A requisite amount of the mixed admixture was then compacted into round tablets of approximately one square inch (6.45 square centimeters) and ⅛ inch (0.32 cm) thickness. Tablets were then broken by hand and screened to particles of 20 to 50 mesh for use in stability studies.

The particles were analyzed for the amount of acephate at zero time by gas chromatography. Zero time concentration of acephate can be conducted either by sampling the particles for acephate concentration at the time the particles are prepared, or alternatively, by placing a sample of the particles at the time they are prepared in storage at 0° C. or less so that the concentration at zero time is preserved. In this latter case, the zero time concentration can be ascertained when the other particle samples are analyzed for acephate concentration. In the examples herein, the zero time concentration was determined by placing the samples in storage at 0° C. or less and then measuring the acephate concentration at the same time other particle samples are removed from accelerated storage conditions.

In any event, the particles are stored in sealed glass bottles maintained at 55° C. (except, of course, for the zero time samples). After storage for 10 and 28 days, the particles were tested for acephate concentration by gas chromatography. The results of these tests are set forth in Table 1B below:

TABLE 1B

| Days in Storage | Amount of Acephate | | | |
|---|---|---|---|---|
| | Form. A | % Loss | Form. B | % Loss |
| 0 | 10.4 | — | 10.1 | — |
| 10 | 10.5 | — | 7.3 | 28 |
| 28 | 10.5 | — | 7.3 | 28 |

As can be seen from the above table, minimizing the presence of processing aids results in superior chemical stability.

B. The second test was conducted as follows:

Different particle formulations containing acephate (Orthene®), ammonium sulfate and varying amounts of processing aids were prepared and tested under accelerated storage conditions. Specifically, admixtures were prepared as shown in Table 2A below:

TABLE 2A

| | Weight Percent in Particles | | | | | | |
|---|---|---|---|---|---|---|---|
| | C | D | E | F | G | H | I |
| Orthene ® Tech[2] | 15.8 | 15.8 | 15.8 | 15.8 | 15.8 | 15.8 | — |
| Hi-Sil 233 | 3.0 | — | 3.0 | — | — | — | — |
| Hi-Sil 135 | — | 3.0 | — | 3.0 | 6.0 | — | 1.0 |
| Magnesium Stearate | — | — | 0.5 | 0.5 | 0.5 | — | 0.5 |
| Ammonium Sulfate | 81.2 | 81.2 | 80.7 | 80.7 | 77.7 | 84.2 | 81.3 |
| Orthene ® 90-S | — | — | — | — | — | — | 17.2 |

[2]Orthene ® Tech contains 97-99% acephate.

The admixtures were then formulated into particles in a manner described above. The particles were stored in sealed glass bottles maintained at 51.7° C. (except for the zero time sample). After storage for 28 days, the particles were tested for acephate concentration by gas chromatography. The results of these tests are set forth in Table 2B below:

TABLE 2B

| Particle | Amount of Initial Acephate Conc. | Amount of Final Acephate Conc. | % Loss |
|---|---|---|---|
| C | 15.1 | 13.9 | 7.9 |
| D | 16.8 | 15.5 | 7.7 |
| E | 16.0 | 14.7 | 8.1 |
| F | 15.8 | 15.5 | 1.9 |
| G | 16.5 | 14.6 | 11.5 |
| H | 15.0 | 15.4 | — |
| I | 15.0 | 14.2 | 5.3 |

The above results demonstrate that when the amount of processing aids used is not minimized, the resulting particles (formulations B and G) containing phosphoroamidothioates are not chemically stable to phosphoroamidothioate degradation, whereas when the amount of processing aids used is minimized, the resulting formulations are stable.

C. The third test was conducted as follows:

A particle formulation containing acephate (Orthene®), ammonium sulfate and 3.5 weight percent of processing aids was prepared and tested under accelerated storage conditions. Specifically, an admixture was prepared as set forth in Table 3A below:

TABLE 3A

| | Weight Percent Formulation J |
|---|---|
| Orthene ® Tech. | 15.3 |
| Hi-Sil 233 | 0.5 |
| Magnesium stearate | 3.0 |
| Ammonium Sulfate | 81.2 |

The admixture was then formulated into particles in a manner described above. However, some problems were encountered in preparing the samples, and low and high assay materials were blended to obtain a 15.4% assay. The particle materials were stored in sealed glass bottles maintained at 51.7° C. (except for the zero time sample). After storage for 14 days, 28 days and 49 days, the particles were tested for acephate concentration by gas chromatography. The results of these tests are set forth in Table 3B below:

TABLE 3B

| Days in Storage | Amount of Acephate | | % Loss |
|---|---|---|---|
| | Particle J | | |
| 0 | 14.65[3] | (14.5/14.8) | — |
| 14 | 12.75[3] | (12.5/13.0) | 13 |
| 28 | 12.125[3] | (12.25/12.0) | 17.2 |
| 49 | 13.8[4] | | 5.8 |

[3] = average of two runs
[4] = one run only

As can be seen from the above results, the invention particles were relatively stable, particularly when the analysis after 49 days is considered. The stability value at 28 days for this example is believed to be in error, because the value at 49 days is significantly better than that at 28 days and further because there were some problems in preparing the particle.

D. A fourth test was conducted as follows:

Particle formulations containing acephate (Orthene®), ammonium sulfate and varying amounts of processing aids were prepared and tested under accelerated storage conditions. Specifically, admixtures were prepared as set forth in Table 4A below:

TABLE 4A

| | Weight Percent in Particle | | |
|---|---|---|---|
| | K | L | M |
| Orthene ® Tech. | 15.3 | 15.3 | 15.3 |
| Hi-Sil 233 | 3.0 | — | — |
| Hi-Sil 135 | — | 3.0 | 1.5 |
| Magnesium stearate | 0.5 | 0.5 | 0.5 |
| Ammonium Sulfate | 81.2 | 81.2 | 82.7 |

The admixtures were then formulated into particles in a manner described above. The particle materials were stored in either a polyethylene rigid container (PE) or an aluminum foil lined bag (Bag) and were maintained at 50° C. (except for the zero time sample). After storage for 14 and 28 days, the particles were tested for acephate concentration by gas chromatography. The results of these tests are set forth in Tables 4B-I and 4B-II below:

TABLE 4B-I

| Days in Storage | Amount of Acephate in Particle Stored in Bag | | | | | |
|---|---|---|---|---|---|---|
| | K | % Loss | L | % Loss | M | % Loss |
| 0 | 16.2 | — | 15.3 | — | 15.2 | — |
| 14 | 15.2 | 6.2% | 15.3 | — | 15.2 | — |
| 28 | 13.9 | 14.2% | 15.0 | 2% | 13.9 | 8.6% |

TABLE 4B-II

| Days in Storage | Amount of Acephate in Particle Stored in PE | | | | | |
|---|---|---|---|---|---|---|
| | K | % Loss | L | % Loss | M | % Loss |
| 0 | 16.2 | — | 15.3 | — | 15.2 | — |
| 14 | 15.2 | 6.2% | 15.2 | 0.6% | 15.0 | 1.3% |
| 28 | 14.1 | 13% | 15.0 | 2.0% | 13.9 | 8.6% |

In regard to the above data, most of the results show that the invention particles are relatively stable. As to why the stability value for formulation K at 28 days is greater than 10% for storage in both the bag and the polyethylene bottle, the inventor considers that possibly the use of a different grade of Hi-Sil material than was used in formulations L and M was the cause of this result (the inventor notes that Hi-Sil 233 has a higher pH than Hi-Sil 135). Since the stability for formulation K at 28 days is inconsistent with most of the other data, it is submitted that the stability result for formulation K at 28 days is anomalous.

E. The fifth test was conducted as follows:

A particle formulation containing acephate (Orthene®), ammonium sulfate and 3.5 weight percent of processing aids was prepared and tested under accelerated storage conditions. Specifically, an admixture was prepared as set forth in Table 5A below:

TABLE 5A

| | Weight Percent Formulation N |
|---|---|
| Orthene ® Tech. | 16.0 |
| Hi-Sil 233 | 3.0 |
| Magnesium stearate | 0.5 |
| Ammonium Sulfate | 80.5 |

The admixture was then formulated into particles in a manner described above. The particle materials were stored in sealed glass bottles maintained at 51.7° C. (except for the zero time concentration).

Three different runs of these particles were prepared and conducted in different glass bottles. Particles from each of these runs were tested for acephate concentration by gas chromatography after storage for 2.1 weeks and 4.1 weeks. Each test was done in duplicate and the results of each of these tests were combined and averaged to provide the composite results set forth in Table 5B below:

TABLE 5B

| Weeks in Storage | Amount of Acephate | |
|---|---|---|
| | Particle N | % Loss |
| 0 | 15.0 | — |
| 2.1 | 14.4[5] | 4% |
| 4.1 | 14.6[6] | 2.7% |

[5] = low of 13.0 in one test and high of 16.0 in one test.
[6] = low of 13.6 in one test and high of 15.1.

The cumulative data presented above demonstrate that the use of ammonium sulfate provides chemical stability to insecticidal phosphoroamidothioate particles containing at most only a small amount of processing aids.

Example 2

The purpose of this example is to demonstrate the significance of employing ammonium sulfate in the insecticidal phosphoroamidothioate particles rather than a seemingly similar sulfate salt, i.e., potassium sulfate.

Two different particle formulations containing acephate (Orthene®) and either ammonium sulfate or potassium sulfate were prepared and tested under accelerated storage conditions. Specifically, admixtures were prepared as set forth in Table 6A below:

TABLE 6A

| | Weight Percent | |
|---|---|---|
| | Particle A | Particle O |
| Orthene ® 90-S | 11.1 | 11.1 |
| Cab-O-Sil M-5 | 0.5 | 0.5 |
| Magnesium stearate | 0.5 | 0.5 |
| Ammonium Sulfate | 87.9 | — |
| Potassium Sulfate | — | 87.9 |

The admixtures were then formulated into particles by first uniformly mixing the admixture. A requisite amount of the mixed admixture was then compacted into round tablets of approximately one square inch (6.45 square centimeters) and ⅛ inch (0.32 centimeters) thickness. Tablets were then broken by hand and screened to particles of 20 to 50 mesh for use in stability studies.

The particles were stored in sealed glass bottles maintained at 55° C. (except for the zero time concentration). After storage for 10 and 28 days, the particles were tested for acephate concentration by gas chromatography. The results of these tests are set forth in Table 6B below:

TABLE 6B

| Days in Storage | Amount of Acephate | | | |
|---|---|---|---|---|
| | Form. A | % Loss | Form. B | % Loss |
| 0 | 10.4 | — | 10.7 | — |
| 10 | 10.5 | — | 9.3 | 13 |
| 28 | 10.5 | — | 9.0 | 16 |

The above results demonstrate that when using a sulfate salt other than ammonium sulfate, particles containing phosphoroamidothioates are not chemically stable with respect to phosphoroamidothioate degradation.

Example 3

The purpose of this example is to demonstrate the significance of employing ammonium sulfate in the insecticidal phosphoroamidothioate particle rather than a seemingly similar ammonium salt, i.e., ammonium phosphate.

Two different particle formulations containing acephate (Orthene®) and either ammonium sulfate or ammonium phosphate were prepared and tested under accelerated storage conditions. Specifically, admixtures were prepared as set forth in Table 7A below:

TABLE 7A

| | Weight Percent | |
|---|---|---|
| | Particle A | Particle P |
| Orthene ® 90-S | 11.1 | 11.1 |
| Cab-O-Sil M-5 | 0.5 | 0.5 |

TABLE 7A-continued

| | Weight Percent | |
|---|---|---|
| | Particle A | Particle P |
| Magnesium stearate | 0.5 | 0.5 |
| Ammonium Sulfate | 87.9 | — |
| Ammonium Phosphate | — | 87.9 |

The admixtures were then formulated into particles by first uniformly mixing the admixture. A requisite amount of the mixed admixture was then compacted into round tablets of approximately one square inch and ⅛ inch thickness. Tablets were then broken by hand and screened to particles of 20 to 50 mesh for use in stability studies.

The particles were stored in sealed glass bottles maintained at 55° C. (except for the zero time concentration). After storage for 10 and 28 days, the particles were tested for acephate concentration by gas chromatography. The results of these tests are set forth in Table 7B below:

TABLE 7B

| Days in Storage | Amount of Acephate | | | |
|---|---|---|---|---|
| | Particle A | % Loss | Particle P | % Loss |
| 0 | 10.4 | — | 10.4 | — |
| 10 | 10.5 | — | 8.5 | 18 |
| 28 | 10.5 | — | 0 | 100 |

The above results demonstrate that when using an ammonium salt other than ammonium sulfate, particles containing phosphoroamidothioates are not chemically stable with respect to phosphoroamidothioate degradation.

Example 4

Insecticidal particles typically can contain materials other than ammonium sulfate in addition to the insecticidal component. Such other materials include, for example, bentonite, diatomaceous earth, and attapulgite. The purpose of this example is to demonstrate the significance of employing ammonium sulfate in the insecticidal phosphoroamidothioate particle rather than substituting other commonly employed particulate materials.

Several particle formulations containing acephate (Orthene ®), ammonium sulfate, optionally another commonly employed particulate material, and optionally one or more processing aids were prepared. Specifically, admixtures were prepared as set forth in Tables 8A-I and 8A-II below:

TABLE 8A-I

| | Weight Percent of Components in Particles | | | | | |
|---|---|---|---|---|---|---|
| | O | R | S | T | U | V |
| Orthene ® Tech | 26.0 | 26.0 | 26.0 | 26.0 | 21.0 | 21.0 |
| Ammonium Sulfate | 74.0 | 40.0 | 40.0 | 40.0 | 40.0 | 40.0 |
| Hi Sil 135 | — | — | — | 3.0 | — | — |
| Magnesium stearate | — | — | — | 0.5 | — | — |
| Bentonite | — | — | — | — | — | — |
| Diatomaceous Earth | — | — | 34.0 | 30.5 | — | 39.0 |
| Attapulgite | — | 34.0 | — | — | 39.0 | — |

TABLE 8A-II

| | Weight Percent of Components in Particles | | | | | |
|---|---|---|---|---|---|---|
| | W | X | Y | Z | AA | BB |
| Orthene ® Tech | 26.0 | 16.0 | 16.0 | 5.5 | 21.0 | 21.0 |
| Ammonium Sulfate | 40.0 | 40.0 | 60.0 | 40.0 | 79.0 | 40.0 |
| Hi Sil 135 | — | — | — | — | — | — |
| Magnesium stearate | — | — | — | — | — | — |
| Bentonite | 34.0 | — | — | — | — | 39.0 |
| Diatomaceous Earth | — | — | — | — | — | — |
| Attapulgite | — | 44.0 | 24.0 | 54.5 | — | — |

The admixtures were then formulated into particles in a manner similar to that described in Example 1.

The particles were stored in sealed glass bottles maintained at 50° C. (except for the zero time concentration). After storage for 28 days, the particles were tested for acephate concentration by gas chromatography. The results of these tests are set forth in Tables 8B-I, 8B-II and 8B-III below:

TABLE 8B-I

| Days in Storage | Amount of Acephate in Particle | | | | | | | |
|---|---|---|---|---|---|---|---|---|
| | O | % Loss | R | % Loss | S | % Loss | T | % Loss |
| 0 | 25.7 | — | 25.6 | — | 25.4 | — | 25.8 | — |
| 28 | 24.9 | 3.1 | 13.0 | 49.2 | 18.4 | 27.6 | 18.4 | 28.7 |

TABLE 8B-II

| Days in Storage | Amount of Acephate in Particle | | | | | | | |
|---|---|---|---|---|---|---|---|---|
| | U | % Loss | V | % Loss | W | % Loss | X | % Loss |
| 0 | 20.0 | — | 21.0 | — | 25.6 | — | 15.8 | — |
| 28 | 11.3 | 44.1 | 15.5 | 26.2 | 17.5 | 31.6 | 9.9 | 37.3 |

TABLE 8B-III

| Days in Storage | Amount of Acephate in Particle | | | | | | | |
|---|---|---|---|---|---|---|---|---|
| | Y | % Loss | Z | % Loss | AA | % Loss | BB | % Loss |
| 0 | 15.4 | — | 5.4 | — | 20.8 | — | 20.7 | — |
| 28 | 11.5 | 25.3 | 0.7 | 87.0 | 18.8 | 9.6 | 10.0 | 51.7 |

The above data demonstrate that use of only ammonium sulfate with the acephate provides for chemically stable particular compositions and that substituting substantial amounts of common particulate materials in place of ammonium sulfate results in significant instability in the particles.

Example 5

The purpose of this example is to demonstrate that higher strength particles that are stable, that will dissolve readily in water and that do not need a binder can be produced by compaction.

Examples containing 93, 84 and 78 weight percent acephate were prepared as set forth in Table 9A below:

TABLE 9A

| | CC | DD | EE | FF | HH | II | JJ | KK | LL |
|---|---|---|---|---|---|---|---|---|---|
| Orthene | 93.0 | 93.0 | 93.0 | 84.0 | 84.0 | 84.0 | 78.0 | 78.0 | 78.0 |
| Ammonium Sulfate | 7.0 | 4.0 | 3.5 | 16.0 | 13.0 | 12.5 | 22.0 | 19.0 | 18.5 |

TABLE 9A-continued

|  | CC | DD | EE | FF | HH | II | JJ | KK | LL |
|---|---|---|---|---|---|---|---|---|---|
| Hi-Sil 135 |  | 3.0 | 3.0 |  | 3.0 | 3.0 |  | 3.0 | 3.0 |
| Mg Stearate |  |  | 0.5 |  |  | 0.5 |  |  | 0.5 |

The ingredients were blended, ground in a rotary blade grinder and remixed. Samples were compacted at 4,000 or 8,000 psig using a Carver press, and the compacted tablets were coarse ground and screened to a particle size range between 20 and 40 mesh. Samples were evaluated or placed into storage in glass bottles.

Evaluations of chemical stability were done by gas chromatography following one month storage at 0° and 50° C.

Samples were evaluated for dissolution properties by adding 2 grams of the compacted particles to 100 ml of water in a 100 ml graduated cylinder. The number of immersions to obtain dissolution of the acephate was recorded.

Particle hardness was measured by an attrition test suitable for determining the resistance of granular materials to attrition during shipping, storing, and handling. In the test, 3.00 grams (±0.01 g) of granular product were subjected to attrition by rolling in a stainless steel container having an interior height of 90 mm, an interior diameter of 52 mm, and an interior wall smoothness of at most 50 RMS (American National Standards Institute) with 14 ball bearings, $\frac{1}{2}$" diameter, polished chrome steel, weighing approximately 8.35 g each, and 40 ball bearings, $\frac{1}{4}$" diameter, polished chrome steel, weighing approximately 0.96 g each. The container was placed in a horizontal position and rotated for 120 seconds ± 1 second. The fine particles generated were separated by screening with a stack consisting of a 10-mesh sieve, a 60-mesh sieve and a bottom pan, and the compacted particles remaining on the 60-mesh screen were weighed to determine the percentage of attrition according to the following formula.

Percent Attrition Loss =

$$\frac{3.00 - (\text{Wt of 60-mesh material in grams})}{3.00} \times 100$$

The results of the tests are set forth in Table 9B below:

TABLE 9B

|  | CC | DD | EE | FF | HH | II | JJ | KK | LL |
|---|---|---|---|---|---|---|---|---|---|
| 4,000 PSIG Compaction Pressure |  |  |  |  |  |  |  |  |  |
| Degradation, 1 mo. 50° C. (%) | 27 | 2 | 10 | 0 | 0 | 1 | 0 | 24 | 12 |
| Dissolution (inversions) | 22 | 8 | 9 | 24 | 6 | 15 | 21 | 11 | 11 |
| Attrition (%) | 98 | 86 | 79 | 98 | 89 | 85 | 98 | 84 | 77 |
| 8,000 PSIG Compaction Pressure |  |  |  |  |  |  |  |  |  |
| Degradation, 1 mo. 50° C. (%) | 5 | 17 | 18 | 13 | 18 | 2 | 8 | 10 | 10 |
| Dissolution (inversions) | 21 | 16 | 26 | 22 | 16 | 29 | 21 | 14 | 33 |
| Attrition (%) | 99 | 97 | 97 | 99 | 97 | 97 | 99 | 97 | 96 |

Degradation, % loss.
Dissolution, Inversions of graduated cylinder to full dissolution.
Attrition, % remaining on 60 mesh sieve, following tumbling in jar with ball bearings.

The bulk of the chemical stability data for the samples compacted at 4,000 psig substantiates the benefit of using ammonium sulfate in admixture with acephate. More degradation was found with the sample compacted at 8,000 psig. The differences between the samples compacted at 4,000 and 8,000 psig are not understood at this time.

The dissolution data provide a relative measure of the dissolution properties. The fewer inversions to complete dissolution of the acephate, the faster the projected dissolution under field use conditions. The data demonstrate that compacted particles dissolve at relatively fast rates. It is considered that samples that show acephate dissolution within 20 inversions should have commercially acceptable dissolution. The particles compacted at 8,000 psig showed generally slower dissolution.

The attrition data demonstrate the utility of compaction in preparing granular sized particles. It is considered that readings of 95% or higher can be representative of a commercially acceptable hardness. At a 4,000 psig compaction pressure, mixtures of acephate plus ammonium sulfate formed the hardest particles, and the addition of hydrated silica or hydrated silica plus magnesium stearate adversely affected the particle hardness. At 8,000 psig, the adverse effects of the additives were overcome by the greater compaction measures.

With adequate compaction pressure, the data demonstrate that a binder is unnecessary.

The data, in general, demonstrate that high strength acephate/ammonium sulfate formulations can be prepared that have adequate chemical stability, adequate hardness and sufficient dissolution rates.

Example 6

These data are provided to show the utility of essentially pure acephate compacted particles and to show the importance of using ammonium sulfate when acephate is to be mixed with a diluent. The data demonstrate the inability to form hard particles when another diluent (hydrated silica) is mixed with acephate. The compositions which were tested are set forth in Table 10A below:

TABLE 10A

|  | Weight Percent | | | | |
|---|---|---|---|---|---|
|  | MM | NN | OO | PP | QQ |
| Orthene ® Tech | 100.0 | — | — | 78.0 | 78.0 |
| Orthene ® 90-S | — | 100.0 | — | — | — |
| Orthene ® 75-S (7) | — | — | 100.0 | — | — |
| Ammonium Sulfate | — | — | — | 22.0 | 19.0 |
| Hi-Sil 135 | — | — | — | — | 3.0 |

(7) Orthene ® 75S contains approximately 78% acephate with the remainder being inerts, primarily silica with approximately 1% surfactant.

The samples were prepared according to the procedures set forth in Example 5, and the results are shown in Table 10B below:

TABLE 10B

|  | MM | NN | OO | PP | QQ |
|---|---|---|---|---|---|
| 4,000 psig compaction pressure | | | | | |
| Degradation, 1 mo., 50° (% loss) | 6 | 0 | 0 | 0 | 24 |
| Dissolution (no. of inversions) | 20 | 6 | >80 | 21 | 11 |
| Attrition (%) | 97 | 57 | 3 | 98 | 84 |
| 8,000 psig compaction pressure | | | | | |
| Degradation, 1 mo., 50° (% loss) | 24 | 2 | 7 | 8 | 10 |
| Dissolution (no. of inversions) | 24 | 13 | >80 | 21 | 14 |
| Attrition (%) | 96 | 92 | 22 | 99 | 97 |

The data demonstrate the utility of forming compacted particles by mixing ammonium sulfate with acephate in cases where acephate is to be mixed with a diluent. The mixtures with ammonium sulfate show acceptable hardness, while the mixtures with silica (without ammonium sulfate) do not meet the hardness standards and would need addition of a binder. Also, the data show that essentially pure acephate compacted particles have good resistance to attrition.

Because the particles of the present invention are chemically stable, use of these particles in methods for controlling insects will lead to superior results as compared with particles heretofore used, insofar as less amounts of insecticidal phosphoroamidothioate will degrade over time.

While the invention has been described in detail and with reference to specific embodiments thereof, it will be apparent to one skilled in the art that various changes and modifications can be made therein without departing from the spirit and scope thereof.

What is claimed is:

1. A method for manufacturing an insecticidal composition, comprising
   (a) mixing components consisting essentially of ammonium sulfate and at least one insecticidal compound of the formula:

$$R-Y \diagdown \overset{O}{\underset{P-N}{\diagup}} \diagup \overset{O}{\underset{\diagdown}{\overset{\|}{C}-R^2}}$$
$$R^1-S \diagup \qquad R^3$$

wherein R and $R^1$ individually are an alkyl, alkenyl or alkynyl group containing up to 6 carbon atoms, $R^2$ is hydrogen, an alkyl group containing 1 to 18 carbon atoms, a cycloalkyl group containing 3 to 8 carbon atoms, an alkenyl group containing 2 to 18 carbon atoms or an alkynyl group containing 3 to 18 carbon atoms, $R^3$ is hydrogen or an alkyl group containing 1 to 6 carbon atoms, and Y is oxygen or sulfur in a mixer to produce a compacted formulation,
   wherein the components being mixed do not include any water;
   (b) compacting the mixture in a compactor to produce a compacted formulation;
   (c) crushing the compacted formulation to form irregularly shaped to spherically shaped compacted particles; and
   (d) screening the compacted particles through a screen to separate oversized particles and undersized particles from particles having a desired particle size.

2. A method for manufacturing as claimed in claim 1, wherein no binder is present in any step.

3. A method for manufacturing as claimed in claim 2, wherein the compacting is at a pressure of at least about 4000 psig.

4. A method for manufacturing as claimed in claim 2, wherein the compacting is at a pressure of at least about 8000 psig.

5. A method for manufacturing as claimed in claim 1, wherein the method further comprises
   (e) crushing the oversized particles to form crushed particles;
   (f) feeding the crushed particles to the screen for screening; and
   (g) recycling the undersized particles to the mixing step for reprocessing.

6. A method for manufacturing as claimed in claim 5, wherein no binder is present in any step.

7. A method for manufacturing as claimed in claim 6, wherein the compacting is at a pressure of at least about 4000 psig.

8. A method for manufacturing as claimed in claim 6, wherein the compacting is at a pressure of at least about 8000 psig.

9. A method for manufacturing a chemically stable insecticidal composition, comprising
   (a) compacting a starting composition consisting essentially of at least one insecticidal compound of the formula:

$$R-Y \diagdown \overset{O}{\underset{P-N}{\diagup}} \diagup \overset{O}{\underset{\diagdown}{\overset{\|}{C}-R^2}}$$
$$R^1-S \diagup \qquad R^3$$

wherein R and $R^1$ individually are an alkyl, alkenyl or alkynyl group containing up to 6 carbon atoms, $R^2$ is hydrogen, an alkyl group containing 1 to 18 carbon atoms, a cycloalkyl group containing 3 to 8 carbon atoms, an alkenyl group containing 2 to 18 carbon atoms or an alkynyl group containing 3 to 18 carbon atoms, $R^3$ is hydrogen or an alkyl group containing 1 to 6 carbon atoms, and Y is oxygen or sulfur in a mixer to produce a compacted formulation,
   wherein the starting composition does not include any water;
   (b) crushing the compacted formulation to form irregularly shaped to spherically shaped compacted particles; and
   (c) screening the compacted particles through a screen to separate oversized particles and undersized particles from particles having a desired particle size.

10. A method for manufacturing as claimed in claim 9, wherein no binder is present in any step.

11. A method for manufacturing as claimed in claim 10, wherein the compacting is at a pressure of at least about 4000 psig.

12. A method for manufacturing as claimed in claim 10, wherein the compacting is at a pressure of at least about 8000 psig.

13. A method for manufacturing as claimed in claim 9, wherein the method further comprises
   (d) crushing the oversized particles to form crushed particles;

(e) feeding the crushed particles to the screen for screening; and (f) recycling the undersized particles to the compacting step for reprocessing.

14. A method for manufacturing as claimed in claim 13, wherein no binder is present in any step.

15. A method for manufacturing as claimed in claim 14, wherein the compacting is at a pressure of at least about 4000 psig.

16. A method for manufacturing as claimed in claim 14, wherein the compacting is at a pressure of at least about 8000 psig.

* * * * *